United States Patent [19]

McEwen et al.

[11] Patent Number: 5,077,366

[45] Date of Patent: Dec. 31, 1991

[54] NOVEL PHOSPHONIC ACID COMPOUNDS AND METHOD OF PREPARATION

[75] Inventors: Gerald K. McEwen, Ashland, Va.; Donald L. Schmidt, Midland, Mich.

[73] Assignee: The Dow Chemical Company, Midland, Mich.

[21] Appl. No.: 661,757

[22] Filed: Feb. 27, 1991

Related U.S. Application Data

[62] Division of Ser. No. 183,853, Apr. 20, 1988, which is a division of Ser. No. 82,758, Aug. 7, 1987, Pat. No. 4,758,384.

[51] Int. Cl.$^5$ ............................................. C08F 230/02
[52] U.S. Cl. .................................... 526/278; 526/347; 526/318.5; 526/328.5; 526/345
[58] Field of Search ........................................ 526/278

[56] References Cited

U.S. PATENT DOCUMENTS

| | | | |
|---|---|---|---|
| 2,439,214 | 4/1948 | Lindsey, Jr. | 526/278 |
| 2,586,885 | 2/1952 | Toy et al. | 428/251 |
| 2,743,261 | 4/1956 | Coover | 526/278 |
| 3,161,667 | 12/1964 | Abramo et al. | 558/125 |
| 3,179,308 | 7/1965 | Stahlhofen | 526/278 |
| 3,385,914 | 5/1968 | Hindersinn et al. | 558/169 |
| 3,468,982 | 9/1969 | Klein et al. | 558/182 |
| 3,684,779 | 8/1972 | Rapko | 526/271 |
| 3,879,498 | 4/1975 | Iliopulos et al. | 558/182 |
| 4,129,710 | 12/1978 | Jin | 526/278 |

FOREIGN PATENT DOCUMENTS

| | | |
|---|---|---|
| 2442428 | 3/1976 | Fed. Rep. of Germany . |
| 2614874 | 10/1977 | Fed. Rep. of Germany . |
| 2918161 | 11/1980 | Fed. Rep. of Germany . |
| 598907 | 3/1978 | U.S.S.R. . |
| 598909 | 3/1978 | U.S.S.R. . |
| 691459 | 10/1979 | U.S.S.R. . |
| 702027 | 12/1979 | U.S.S.R. . |

*Primary Examiner*—Joseph L. Schofer
*Assistant Examiner*—M. Nagumo

[57] ABSTRACT

Novel phosphonic acid-containing compounds such as (2-(4-ethylphenyl)ethenyl)-phosphonic acid and esters thereof are disclosed. A method preparation of the phosphonic acids comprising contacting a diethylenically unsaturated aromatic compound and phosphorus pentachloride in the present of sulfur dioxide is also disclosed. The compounds of this invention are useful as monomers for the preparation of polymers having enhanced anti-corrosive properties.

11 Claims, No Drawings

NOVEL PHOSPHONIC ACID COMPOUNDS AND METHOD OF PREPARATION

Cross-Reference to Related Applications

This application is a divisional of copending application Ser. No. 07/183,853, filed Apr. 20, 1988, which is a divisional of application Ser. No. 07/082,758, filed Aug. 7, 1987, now U.S. Pat. No. 4,758,384.

BACKGROUND OF THE INVENTION

This invention relates to phosphorus-containing compounds and to a method for their preparation.

Phosphorus-containing compounds as well as the polymers prepared therefrom are known in the art. Examples of such compounds are the phosphorus-containing vinylidene aromatic monomers described in U.S. Pat. No. 3,161,667 which are useful in the preparation of flame-resistant polymers. These compounds include organic phosphinites, phosphonites and phosphites. Organic phosphonates having utility in the preparation of fire-retardant polymers are disclosed in U.S. Pat. No. 3,468,982. Other organic phosphonates having utility in the preparation of polyesters and polyurethanes are disclosed in U.S. Pat. No. 3,385,914.

One of the problems associated with known phosphorus-containing monomers is their tendency to hydrolyze in the presence of water which leads to the degradation of polymers prepared from such monomers. Thus, it would be desirable to prepare a phosphorus-containing monomer which is hydrolytically stable. Further, it would be desirable to have a process for the preparation of such monomers that utilizes readily available starting materials and operates under mild reaction conditions.

SUMMARY OF THE INVENTION

One aspect of this invention is a novel compound comprising an aromatic ring which has two ethylenically unsaturated substituents, one of which contains a phosphonate or a phosphonic acid moiety. The novel compound of this invention may or may not have additional substituents.

In another aspect, this invention is a method of preparing an aromatic compound which has two ethylenically unsaturated substituents, one of which contains a phosphonic acid moiety which comprises contacting a diethylenically unsaturated aromatic compound with phosphorus pentachloride under reaction conditions sufficient to produce the diethylenically unsaturated aromatic phosphonic acid.

In yet another aspect, this invention is a polymeric composition comprising the novel compound of this invention.

The novel compounds of the present invention are hydrolytically stable and are useful as monomers in the preparation of polymers with anti-corrosive properties. The phosphonic acid group allows a wide variety of interactions between the compound and metals, metal ions and ores.

DETAILED DESCRIPTION OF THE INVENTION

The novel compound of this invention comprises an aromatic ring to which is bonded two ethylenically unsaturated radicals one of which contains a phosphonate or a phosphonic acid moiety bonded to the carbon beta to the ring. It is preferred that the ethylenically unsaturated radicals are para to each other. The aromatic compound may have additional inert substituents either on the ring structure or on the ethylenically unsaturated radicals. In this context, inert substituents are those which do not interfere with the formation of the desired phosphonic acids or with the use of phosphonic acids or phosphonates in their interaction with metals or in polymerization processes. Examples of such inert substituents are straight or branched chain $C_{1-12}$ alkyl substituents such as methyl, ethyl, propyl, butyl, isopropyl, pentyl, and the like.

In a preferred form, the novel compounds of this invention correspond to the formula

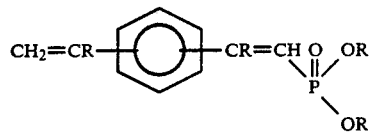

wherein R is independently in each occurrence hydrogen or $C_{1-12}$ alkyl. It is preferred that R be independently in each occurrence lower alkyl such as methyl, ethyl or propyl or hydrogen and most preferred that R be hydrogen in each instance. It is preferred that the two ethylenically unsaturated moieties be para from each other. The most preferred embodiment of the novel compound of this invention is (2-(4-ethenylphenyl)ethenyl)phosphonic acid.

The phosphonic acid compounds of this invention are made by the reaction of phosphorus pentachloride with a diethylenically unsaturated aromatic compound under an inert atmosphere. Sulfur dioxide is added to the reaction mixture which is then concentrated under vacuum. The resulting solution is added to ice water to promote the separation of an organic layer. The aqueous and organic layers are separated and then the organic layer is concentrated and yields white crystals of a phosphonic acid which are isolated by conventional means.

The phosphonates may be readily prepared from the phosphonic acid by contacting the acid with an alkanol under reaction conditions to produce the desired phosphonate. Alkanols useful in this process include $C_{1-12}$ alkanols such as methanol, ethanol and propanol.

The reactants useful in the practice of this invention are a diethylenically unsaturated aromatic compound and a phosphorus-containing compound which will, when contacted with the aromatic compound, form the ethylenically unsaturated aromatic phosphonic acids of this invention. Phosphorus pentachloride is the preferred phosphorus containing compound. A preferred diethylenically unsaturated aromatic compound is divinylbenzene. The diethylenically unsaturated aromatic compound reactant may or may not have one or more inert substituents. Examples of inert substituents include straight or branched chain $C_{1-12}$ alkyls. The reactants used in the process of this invention are well-known and are available commercially.

The reactants may be contacted in any order and relative amounts which will permit the reaction to proceed. It is preferred to first add the diethylenically unsaturated aromatic compound to the solvent; then add the phosphorus pentachloride and acetonitrile or other polar solvent; and, then add sulfur dioxide. The preferred mole ratio of phosphorus pentachloride to diethylenically unsaturated aromatic compound is from about 10:1 to about 1:1 and more preferably from about 2:1 to 1:1. It is most preferred to be about 1:1.

The reaction may be conducted at any temperature at which the reaction will proceed. It is preferred that the reaction take place at a temperature no lower than about $-10°$ C. and no greater than about 75° C. It is more preferred to cool the reactants prior to the addition of the phosphorus pentachloride. It is most preferred to cool the reactants to about 0° C. prior to the addition of the phosphorus pentachloride and then allow the reaction mixture to return to no greater than about 30° C. for the duration of the reaction process.

The reaction may be conducted at superatmospheric or subatmospheric pressure, but is conducted at ambient pressure for the sake of convenience.

A solvent is advantageously used in the practice of this invention. It is preferred to use a nonpolar solvent. Examples of such solvents are aliphatic or cyclic hydrocarbons such as hexane, cyclohexane and methylene chloride; and aromatic solvents such as toluene, benzene, ethylbenzene and the like. It is more preferred to use an aromatic hydrocarbon solvent and it is most preferred to use toluene as a solvent. Any amount of solvent which will allow the reaction to proceed may be used. It is preferred to use from between about 10 volumes of solvent per volume of diethylenically unsaturated aromatic compound reactant and about 30 volumes of solvent per volume of diethylenically unsaturated aromatic compound reactant. It is more preferred to use from about 15 volumes of solvent to about 20 volumes of solvent per volume of diethylenically unsaturated aromatic compound reactant used.

In addition to the inert aromatic solvent, it is preferred to use a small amount of a polar solvent. Without wishing to be bound by any theory, it is speculated that the small amount of polar solvent serves to stabilize the intermediates formed in the process of this invention. Examples of polar solvents useful in the practice of this invention include dimethylsuflfoxide, methanol and acetonitrile. It is preferred to use acetonitrile. Any amount of the polar solvent which will allow the process of this invention to function may be used. A molar ratio of polar solvent to diethylenically unsaturated aromatic compound of no more than about 10:1 and no less than about 0.5:1 is preferred. It is more preferred to use the polar solvent in a molar ratio of about 1:1 based on the diethylenically unsaturated aromatic compound.

Sulfur dioxide is used to facilitate the process of this invention. Without wishing to be bound by any theory, it is speculated that the sulfur dioxide reacts with an intermediate halophosphorinane to form a corresponding phosphonyl halide which then goes on to be hydrolyzed to the desired phosphonic acid. The sulfur dioxide may be used in any amount which will promote the reaction. It is preferred to use the sulfur dioxide in a slight molar excess based on the amount of diethylenically unsaturated aromatic compound reactant used. The mole ratio of sulfur dioxide to diethylenically unsaturated aromatic compound may preferably range from about 10:1 to about 1:1 and is more preferred to be between about 2:1 and 1:1. It is most preferred to be between about 1.5:1 and 1:1.

The reaction is preferably conducted under an inert atmosphere. Examples of inert atmospheres include argon, helium and nitrogen. It is most preferred that the reaction be conducted under a nitrogen atmosphere.

In a preferred embodiment, divinylbenzene, toluene and acetonitrile are charged to a reaction vessel and cooled in an ice bath. Phosphorus pentachloride is added all at once. The solution is kept under a nitrogen atmosphere supplied by a flush stream, allowed to come to room temperature and stirred overnight. Sulfur dioxide is condensed in a small graduated cylinder and then allowed to boil and fed into the divinylbenzene-phosphorus pentachloride solution through the nitrogen flush stream. The resulting solution is concentrated under vacuum and then added to an ice/water mixture. The organic and aqueous layers separate and crystals of the phosphonic acid form in the organic layer and are isolated by conventional means.

The product so obtained can be polymerized by conventional vinyl polymerization techniques well known in the art such as free radical polymerization, as taught, for example, in U.S. Pat. No. 4,054,733 hereby incorporated by reference. These processes may be conducted in continuous or batch procedures as appropriate. The 1,2-ethylenically unsaturated phosphonic acid containing monomers may be homopolymerized or copolymerized with one or more compounds which contain a polymerizable ethylenically unsaturated moiety.

Any compound containing a polymerizable ethylenically unsaturated moiety may be useful as a comonomer in the practice of this invention. Examples of such compounds include aromatic compounds substituted with 1,2-ethylenically unsaturated moieties such as, styrene, vinyl toluene, tert-butylstyrene; $\alpha$, $\beta$-ethylenically unsaturated acids such as acrylic acid and methylacrylic acid; alkyl ester of $\alpha$, $\beta$-ethylenically unsaturated monocarboxylic acids, such as methyl acrylate, ethyl acrylate, and methyl methacrylate; vinyl halides, such as vinyl chloride and vinyl bromide; vinyl ethers, such as vinyl methyl ether and vinyl ethyl ether; vinyl ketones, such as vinyl methyl ketone and vinyl ethyl ketone; vinylidene halides such as vinylidene chloride and vinylidene bromide; and the like.

The polymers and copolymers so produced show enhanced anti-corrosive properties.

The following illustrative example is given, not to limit the scope of the invention, but to more clearly explain it. Unless stated otherwise, all parts and percentages are given by weight.

EXAMPLE

Preparation of (2-(4-ethenylphenyl) ethenyl)-phosphonic acid

A 2-liter round-bottom, 3-neck flask is fitted with a mechanical stirrer, a solids addition funnel, a nitrogen inlet, and a thermometer. The flask is charged with 1200 ml of toluene and 65.0 g of 95 percent divinylbenzene and cooled in an ice bath. A 104.25-g portion of $PCl_5$ and 20 g of acetonitrile are slowly added. The mixture is then stirred overnight at room temperature under a slow $N_2$ flush.

A 23.5-ml portion of $SO_2$ is condensed in a small graduated cylinder. The cylinder is fitted with an outlet and tubing which is connected to a hypodermic needle. The needle is inserted into the $N_2$ flush line and the $SO_2$ is allowed to warm and boil and to transfer over to the reaction flask over a period of about two hours. A clear yellow solution is produced which is then concentrated under vacuum to approximately one-half of its original volume. The solution is then added slowly to approximately 500 ml of stirred ice/water. This mixture is stirred for one hour and then transferred to a 2-liter separatory funnel and left undisturbed overnight. White crystals form in the organic layer. Both the aqueous and organic layers are drained off and the crystals are washed with a small amount of toluene. The crystals in the separatory funnel are then dried in a gentle $N_2$ stream and then removed from the separatory funnel and dried under high vacuum. A 3.5-g portion of the product, shown below, is obtained and is characterized by elemental analysis and shows 55.1 percent carbon and 5.38 percent hydrogen.

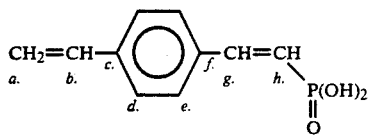

The product is also characterized by NMR and shows the following:

$31_P$: $\delta = 16.7$ ppm; doublet of doublets; $J = 17$ Hz; $J = 22$ Hz.

$13_C$: $\delta$: a. 114.8; b. 136.0; c. 138.6; d. 126.5 or 127.6; e. 127.6 or 126.5; f. 143.9 $^3J_{PC} = 6.1$ Hz; g. 124.8 $^2J_{PC} = 23$ Hz; h. 118.4 $^1J_{PC} = 188$ Hz.

We claim:

1. An addition homopolymer of a compound which comprises an aromatic ring to which are bonded two ethylenically unsaturated substituents wherein one of the ethylenically unsaturated substituents has a moiety selected from the group consisting of phosphonate and phosphonic acid that is bonded to a carbon beta to the aromatic ring, said beta carbon having an ethylenically unsaturated bond to the carbon alpha to said aromatic ring.

2. An addition copolymer of (1) a first compound which comprises an aromatic ring to which are bonded two ethylenically unsaturated substituents wherein one of the ethylenically unsaturated substituents has a moiety selected from the group consisting of phosphonate and phosphonic acid that is bonded to a carbon beta to the aromatic ring, said beta carbon having an ethylenically unsaturated bond to the carbon alpha to said aromatic ring, and (2) one or more additional ethylenically unsaturated compounds.

3. The addition homopolymer of claim 1 wherein the compound corresponds to the formula:

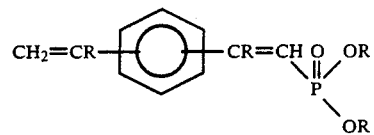

wherein R is independently in each occurrence hydrogen or $C_{1-12}$ alkyl.

4. The addition homopolymer of claim 3 wherein R is independently in each occurrence selected from hydrogen, methyl, ethyl, or propyl.

5. The addition homopolymer of claim 3 wherein R is hydrogen.

6. The addition homopolymer of claim 3 wherein the two ethylenically unsaturated substituents are para to each other.

7. The addition copolymer of claim 2 wherein the first compound corresponds to the formula:

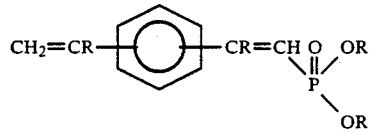

wherein R is independently in each occurrence hydrogen or $C_{1-12}$ alkyl.

8. The addition copolymer of claim 7 wherein R is independently in each occurrence selected from hydrogen, methyl, ethyl, or propyl.

9. The addition copolymer of claim 7 wherein R is hydrogen.

10. The addition copolymer of claim 7 wherein the two ethylenically unsaturated substituents are para to each other.

11. The addition copolymer of claim 2 wherein the additional ethylenically unsaturated compounds are selected from styrene, vinyl toluene, tert-butylstyrene, acrylic acid, methacrylic acid, methyl acrylate, ethyl acrylate, methyl methacrylate, vinyl chloride, vinyl bromide, vinyl methyl ether, vinyl ethyl ether, vinyl methyl ketone, vinyl ethyl ketone, vinylidene chloride, and vinylidene bromide.

* * * * *